(12) United States Patent
Miller et al.

(10) Patent No.: US 9,040,711 B2
(45) Date of Patent: May 26, 2015

(54) PROCESSES FOR THE PREPARATION OF 3,5-DISUBSTITUTED-1,2,4-OXADIAZOLES

(71) Applicant: Monsanto Technology LLC, St. Louis, MO (US)

(72) Inventors: William Harold Miller, Glendale, MO (US); Charles Richard Graham, St. Peters, MO (US); David Louis Brown, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 13/933,616

(22) Filed: Jul. 2, 2013

(65) Prior Publication Data

US 2014/0039197 A1 Feb. 6, 2014

Related U.S. Application Data

(60) Provisional application No. 61/783,466, filed on Mar. 14, 2013, provisional application No. 61/777,210, filed on Mar. 12, 2013, provisional application No. 61/667,361, filed on Jul. 2, 2012.

(51) Int. Cl.
*C07D 271/06* (2006.01)
*C07D 413/04* (2006.01)

(52) U.S. Cl.
CPC ............ *C07D 413/04* (2013.01); *C07D 271/06* (2013.01)

(58) Field of Classification Search
CPC .................................................. C07D 271/06
USPC ......................................... 548/131; 514/364
See application file for complete search history.

(56) References Cited

U.S. PATENT DOCUMENTS

| | | | |
|---|---|---|---|
| 3,192,103 A | 6/1965 | Sousa et al. |
| 3,211,742 A | 10/1965 | Lanaers et al. |
| 3,218,331 A | 11/1965 | Eloy |
| 3,227,725 A | 1/1966 | Eloy et al. |
| 3,264,318 A | 8/1966 | Eloy |
| 5,112,841 A | 5/1992 | Matsubara et al. |
| 6,992,096 B2 | 1/2006 | Karp et al. |
| 7,041,685 B2 | 5/2006 | Cai et al. |
| 7,678,922 B2 | 3/2010 | Almstead et al. |
| 7,799,812 B2 | 9/2010 | Albert et al. |
| 2003/0055085 A1 | 3/2003 | Wagenen et al. |
| 2005/0075375 A1 | 4/2005 | Vourloumis et al. |
| 2008/0113961 A1 | 5/2008 | Nishi et al. |
| 2008/0269236 A1 | 10/2008 | Ji et al. |
| 2009/0048311 A1 | 2/2009 | Williams et al. |
| 2010/0048648 A1 | 2/2010 | Bolli et al. |
| 2010/3005086 | 12/2010 | Gopalakrishnan et al. |
| 2011/0311459 A1 | 12/2011 | Amari et al. |
| 2012/0022109 A1 | 1/2012 | Quattropani et al. |

FOREIGN PATENT DOCUMENTS

| | | |
|---|---|---|
| GB | 924608 | 4/1963 |
| JP | 2008120794 | 5/2008 |
| WO | 8706249 A1 | 11/1987 |
| WO | 9857969 A1 | 12/1998 |
| WO | 2004058253 A1 | 7/2004 |
| WO | 2009023721 A1 | 2/2009 |
| WO | 2009041972 A1 | 4/2009 |
| WO | 2009080730 A1 | 7/2009 |
| WO | 2009148452 A1 | 12/2009 |
| WO | 2010054763 A1 | 5/2010 |
| WO | 2010072352 A1 | 7/2010 |
| WO | 2010093650 A2 | 8/2010 |
| WO | 2010142628 A1 | 12/2010 |
| WO | 2011085406 A1 | 7/2011 |
| WO | 2011141326 A1 | 11/2011 |
| WO | 2012012477 A1 | 1/2012 |
| WO | 2012030887 A1 | 3/2012 |

OTHER PUBLICATIONS

Caumul, 2011, Journal of Environmental Research and Development, vol. 5, No. 3, p. 495-508.*
Voron'Ko et al., "Synthesis of 3,5-Disubstituted 1,2,4-Oxadiazoles and Reactivity of N-Hydroxybenzmnidines," 2006, Russian Federation, 49:60-63. 11 pages.
Chiou, S., et al., "A Simplified Procedure for Preparing 3,5-disubstituted-1,2,4-oxadiazoles by Reaction of Amidoximes with Acyl Chlorides in Pyridine Solution," 1989, J Het Chem , 26:125-128.
Diana, G. D., et al., "Oxadiazoles as Ester Bioisosteric Replacements in Compounds Related to Disoxaril. Antirhinovirus Activity," 2004, J Med Chem, 1994, 37:2421-2436.
Hauqwitz, R.D., et al., "Antiparasitic Agents. 6. Synthesis and Anthelmintic Activities of Novel Isothiocyanatophenyl-1,2,4-oxadiazoles," 1985, J Med Chem, 28:1234-1241.
Kemnitzer, W., et al., "Discovery of 3-aryl-t-aryl-1,2,4-oxadiazoles as a New Series of Apoptosis Inducers. 1. Identification of More Aqueous Soluble Analogs as Potential Anticancer Agents," 2009, Bioorg Med Chem Lett, 19:4410-4415.
Zhang, H.Z, et al., "Discovery and Structure—Activity Relationship of 3-aryl-5-aryl-1,2,4-oxadiazoles as a New Series of Apoptosis Inducers and Potential Anticancer Agents," 2005, J Med Chem, 48:5215-5223.
Andersen, K.E., et al., "Oxadiazoles as Bioisosteric Transformations of Carboxylic Functionalities. II," 1996, Eur J. Med Chem, 31/417-425, 9 pages.

(Continued)

*Primary Examiner* — Rebecca Anderson
*Assistant Examiner* — Karen Cheng
(74) *Attorney, Agent, or Firm* — Senniger Powers LLP; Molly B. Edwards

(57) ABSTRACT

Provided herein are processes for the preparation of 3,5-disubstituted-1,2,4-oxadiazoles and salts thereof comprising reacting a N-hydroxyamidine with an acyl chloride in a reaction mixture comprising a water-immiscible organic solvent and an aqueous base at relatively low reaction temperatures.

45 Claims, No Drawings

(56) References Cited

OTHER PUBLICATIONS

Gangloff, A.R., et al., "Synthesis of 3,5-disubstituted-1,2,4-oxadiazoles Using Tetrabutylammonium Fluoride as a Mild and Efficient Catalyst," 2001, Tetrahedron Ltrs, 42:1441-1443, 3 pages.

Herbet, N., et al., "Synthesis of Exadiazoles on Solid Support," 1999, Tetrahedron Ltrs, 40:8547-8550, 4 pages.

Kayukova, L.A., et al., "Unexpectedly Facile Heterocyclization of O-Benzoyl-β-Piperidinopropioamidoxime in Dimethyl Sulfoxide," 1999, Chem Hetero Comp, 35/5:630-631, 2 pages.

Korbonits, D., et al., "Synthesis of Heterocycles from Aminoamide Oximes#," 1994, Heterocycles, 37/3:2051-2068, 18 pages.

Lukyanov, S.M., et al., "Synthesis of Sterically Hindered 3-(azolyl)pyridines," 2009, Arkivoc, (iv), 21-45, 25 pages.

Ooi, N.S., et al., "Formation and Thermal Reaction of O-(N-Acetylbenzimidoyl)benzamidoxime: Comparison with the Formation of 3,5-Disubstituted 1,2,4-Oxadiazoles from O-Acetylarylamidoximes and O-Aroylacetamidoximes," 1980, J Chem Soc, Perkin Trans II, 1792-1799, 8 pages.

Written Opinion issued in PCT/US2013/049060, Dec. 17, 2013, 4 pages.

International Search Report issued in PCT/US2013/049060, Dec. 17, 2014, 4 pages.

* cited by examiner

PROCESSES FOR THE PREPARATION OF 3,5-DISUBSTITUTED-1,2,4-OXADIAZOLES

This application claims benefit of U.S. provisional application Ser. No. 61/667,361, filed Jul. 2, 2012, U.S. provisional application Ser. No. 61/777,210, filed Mar. 12, 2013 and U.S. provisional application Ser. No. 61/783,466, filed Mar. 14, 2013, the entire disclosures of which are incorporated herein by reference.

FIELD

Provided herein are processes for the preparation of biologically active 3,5-disubstituted-1,2,4-oxadiazoles or salts thereof that are useful, for example, in the control of nematodes.

BACKGROUND 1,2,4-Oxadiazoles, and in particular, 3,5-disubstituted-1,2,4-oxadiazoles, have been shown to have biological activity in pharmaceutical and agricultural fields. For example, 3,5-disubstituted-1,2,4-oxadiazoles are disclosed as disease suppression and treatment agents (U.S. Pat. No. 6,992,096), as therapeutic agents for hepatitis C (Pub. No. US 2005/0075375 A1), and for nematode control in agriculture (Pub. No. US 2009/0048311 A1).

3,5-Disubstituted-1,2,4-oxadiazoles can be prepared in a number of ways. One is preparation of 3,5-disubstituted-1,2,4-oxadiazoles via reaction of an aryl amide oxime and an acyl chloride (Pub. No. US 2008/0269236 A1, U.S. Pat. No. 7,678,922, Pub. No. US 2008/0113961 A1, JP 2008120794 and Bioorg. Med Chem Lett. 19, 4410). Another method for preparation of 3,5-disubstituted-1,2,4-oxadiazoles is reaction of a benzamide oxime or propionamidoxime with a carboxylic acid or ester (WO 2011/141326, WO 2012/012477, and WO 2011/085406). Other routes to 3,5-disubstituted-1,2,4-oxadiazoles include reaction of a benzamide with a Weinreb amide (Pub. No. US 2010/0048648 A1) and reaction of a hydroxyamyl halide and a nitrile (U.S. Pat. No. 3,211,742).

While methods for preparing 3,5-disubstituted-1,2,4-oxadiazoles exist, alternative routes that may result in a more efficient synthesis are highly desirable. In particular, synthetic processes with fewer isolation steps and/or solvents can be more efficient and less expensive. In addition, processes that reduce and/or eliminate solids handling, reduce reaction time and/or use fewer reaction intermediates can significantly reduce capital equipment expenditures in large scale manufacturing. Finally, the use of milder reaction conditions (e.g. lower temperatures) may prevent degradation of desired intermediates and products resulting in fewer unwanted side products and ultimately a better product purity profile.

Citation of any reference above is not to be construed as an admission that such reference is prior art to the present application.

SUMMARY

Provided herein are processes for the preparation of 3,5-disubstituted-1,2,4-oxadiazoles and salts thereof. For example, the processes described herein are useful for preparing a 3,5-disubstituted-1,2,4-oxadiazole of Formula (Ia) or (Ib),

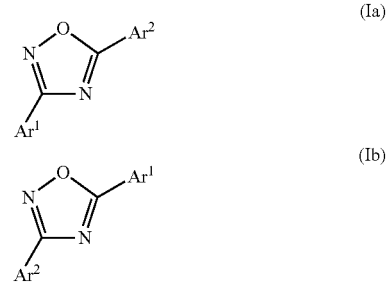

wherein $Ar^1$ is phenyl, pyridyl, pyrazyl, oxazolyl or isoxazolyl, each of which can be optionally independently substituted with one or more substituents e.g. alkyl, haloalkyl, alkoxy, haloalkoxy, halogen, acyl, ester, and nitrile; and $Ar^2$ is thienyl, furanyl, oxazolyl, isoxazolyl, or phenyl, each of which can be optionally independently substituted with one or more substituents e.g. fluorine, chlorine, $CH_3$, and $OCF_3$. In one embodiment, the process comprises reacting a N-hydroxyamidine of Formula (IIa) or (IIb), respectively, or a tautomeric form thereof, wherein $Ar^1$ and $Ar^2$ are defined as above,

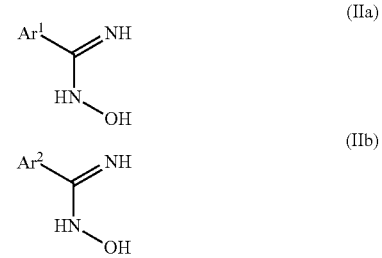

with an acyl chloride of Formula (IIIa) or (IIIb), respectively, wherein $Ar^1$ and $Ar^2$ are defined as above,

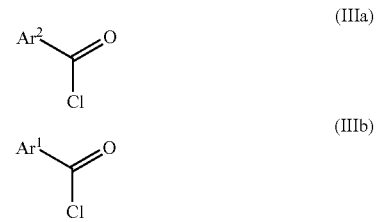

in a reaction mixture comprising a water-immiscible organic solvent and an aqueous base and the temperature of the reaction mixture is no greater than about 85° C.

DETAILED DESCRIPTION

The present disclosure is directed to improved processes for the preparation of 3,5-disubstituted-1,2,4-oxadiazoles and salts thereof. Various embodiments of the process enable greater ease of production, milder reaction conditions, reduced reaction time cycles, fewer reaction intermediates, and/or significantly reduced capital equipment requirements.

Generally, the processes described herein are useful for preparing a 3,5-disubstituted-1,2,4-oxadiazole of Formula (Ia) or (Ib) or a salt thereof,

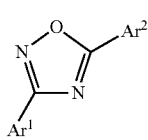
(Ia)

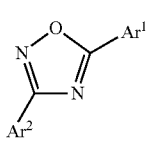
(Ib)

wherein Ar$^1$ is phenyl, pyridyl, pyrazyl, oxazolyl or isoxazolyl, each of which can be optionally independently substituted with one or more substituents. In one embodiment Ar$^1$ is optionally independently substituted with one or more substituents selected from the group consisting of alkyl, haloalkyl, alkoxy, haloalkoxy, halogen, acyl, ester, and nitrile each of which can be optionally independently substituted. In one embodiment, Ar$^1$ is optionally independently substituted with one or more substituents selected from the group consisting of halogen, CF$_3$, CH$_3$, OCF$_3$, OCH$_3$, CN and C(H)O. Ar$^2$ is thienyl, furanyl, oxazolyl, isoxazolyl, or phenyl, each of which can be optionally independently substituted. In one embodiment, Ar$^2$ is optionally independently substituted with one or more substituents selected from the group consisting of fluorine, chlorine, CH$_3$, and OCF$_3$.

For example, in some embodiments, Ar$^1$ is unsubstituted phenyl. In other embodiments, Ar$^1$ is monosubstituted phenyl wherein the substituent is a halogen. In still other embodiments, Ar$^1$ is a disubstituted chloroalkylphenyl. In some embodiments, Ar$^2$ is substituted thienyl or substituted furanyl. In some embodiments, Ar$^2$ is unsubstituted thienyl or unsubstituted furanyl.

In some embodiments, the 3,5-disubstituted-1,2,4-oxadiazole is a compound of Formula (Ia-i) or a salt thereof,

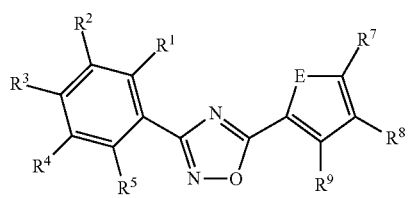
(Ia-i)

wherein R$^1$ and R$^5$ are independently selected from hydrogen, CH$_3$, F, Cl, Br, CF$_3$ and OCF$_3$; R$^2$ and R$^4$ are independently selected from hydrogen, F, Cl, Br, and CF$_3$; R$^3$ is selected from hydrogen, CH$_3$, CF$_3$, F, Cl, Br, OCF$_3$, OCH$_3$, CN, and C(H)O; R$^7$ and R$^8$ are independently selected from hydrogen and fluorine; R$^9$ is selected from hydrogen, F, Cl, CH$_3$, and OCF$_3$; and E is O, N or S.

Non-limiting examples of 3,5-disubstituted-1,2,4-oxadiazoles that can be prepared in accordance with the present disclosure include 3-phenyl-5-(2-thienyl)-1,2,4-oxadiazole of Formula (Ia-ii),

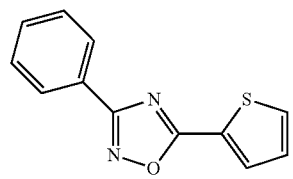
(Ia-ii)

3-(4-chlorophenyl)-5-(2-furanyl)-1,2,4-oxadiazole of Formula (Ia-iii),

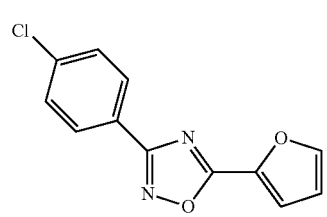
(Ia-iii)

3-(4-chloro-2-methylphenyl)-5-(2-furanyl)-1,2,4-oxadiazole of Formula (Ia-iv),

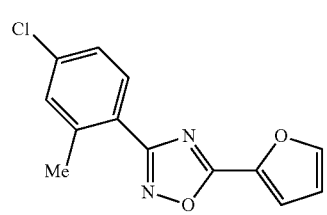
(Ia-iv)

3-phenyl-5-(2-furanyl)-1,2,4-oxadiazole of Formula (Ia-v),

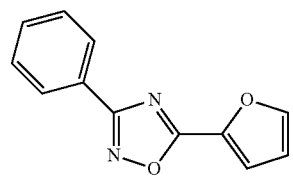
(Ia-v)

3-(4-bromophenyl)-5-(furan-3-yl)-1,2,4-oxadiazole of Formula (Ia-vi) and,

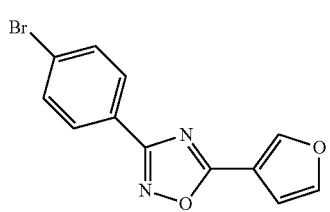
(Ia-vi)

3-(2,4-difluorophenyl)-(thiophen-3-yl)-1,2,4-oxadiazole of Formula (Ia-vii).

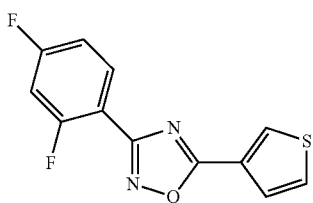

(Ia-vii)

In further embodiments, the 3,5-disubstituted-1,2,4-oxadiazole is a compound of Formula (Ib-i) or a salt thereof,

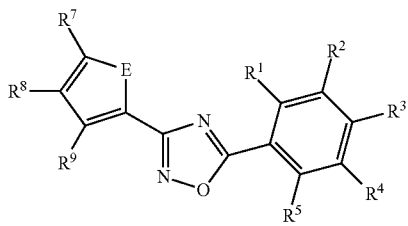

(Ib-i)

wherein $R^1$ through $R^5$, $R^7$ through $R^9$ and E are defined as above.

Additional non-limiting examples of 3,5-disubstituted-1,2,4-oxadiazoles that can be prepared in accordance with the present disclosure include 3-(thiophen-2-yl)-5-(p-tolyl)-1,2,4-oxadiazole of Formula (Ib-ii),

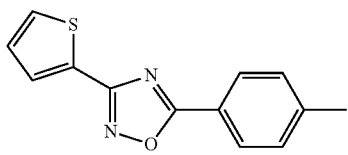

(Ib-ii)

5-(3-chlorophenyl)-3-(thiophen-2-yl)-1,2,4-oxadiazole of Formula (Ib-iii) and,

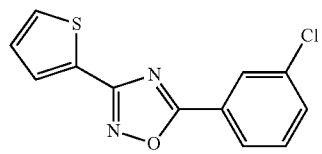

(Ib-iii)

5-(4-chloro-2-methylphenyl)-3-(furan-2-yl)-1,2,4-oxadiazole of Formula (Ib-iv).

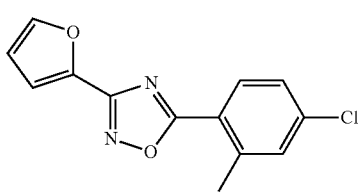

(Ib-iv)

Further representative 3,5-disubstituted-1,2,4-oxadiazoles that can be prepared in accordance with the present disclosure are described in Pub. No. US 2009/0048311 A1, the entire contents of which are incorporated herein by reference.

In various embodiments, the process comprises reacting a N-hydroxyamidine of Formula (IIa) or (IIb), or a tautomeric form thereof,

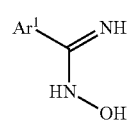

(IIa)

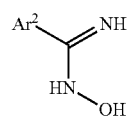

(IIb)

wherein $Ar^1$ and $Ar^2$ are defined as above, with an acyl chloride of Formula (IIIa) or (IIIb), respectively,

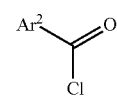

(IIIa)

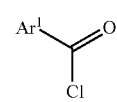

(IIIb)

wherein $Ar^1$ and $Ar^2$ are defined as above. The condensation reaction of the N-hydroxyamidine with the acyl chloride is conducted in a reaction mixture comprising an organic solvent and an aqueous base. Without being bound to a particular theory, in some embodiments, the reaction of the N-hydroxyamidine and the acyl chloride is believed to produce an oxime ester intermediate of Formula (IVa) or (IVb), a salt thereof, or a tautomeric form thereof,

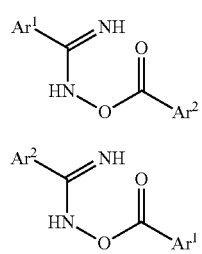

(IVa)

(IVb)

wherein $Ar^1$ and $Ar^2$ are defined as above. As described in greater detail below, the presence of an aqueous base facilitates cyclization of the oxime ester at relatively low temperatures to produce the 3,5-disubstituted-1,2,4-oxadiazole product. In an embodiment, the condensation and/or cyclization reaction is allowed to proceed directly to the final 3,5-disubstituted-1,2,4-oxadiazole product, without isolation or purification of the oxime ester intermediate. In other embodiments, the oxime ester intermediate, or a portion thereof, may be isolated and/or purified prior to formation of the 3,5-disubstituted-1,2,4-oxadiazole product.

In accordance with various embodiments, solvents used to form the reaction mixture are selected on the basis of one or more criteria, to facilitate simplification and overall economics of the process. In some embodiments, the organic solvent employed is capable of solubilizing the N-hydroxyamidine of Formula (IIa) or (IIb) and the 3,5-disubstituted-1,2,4-oxadiazole product of Formula (Ia) or (Ib). In some embodiments the organic solvent is capable of solubilizing the intermediate oxime ester of Formula (IVa) or (IVb) as well. Use of an organic solvent to solubilize the N-hydroxyamidine starting material as well as the oxime ester intermediate and the 3,5-disubstituted-1,2,4-oxadiazole product reduces or eliminates the need for isolation of the N-hydroxyamidine and/or the oxime ester, and reduces or eliminates the need for a solvent switch prior to cyclization to form the 3,5-disubstituted-1,2,4-oxadiazole product. In various embodiments, the organic solvent may advantageously be used to transfer the N-hydroxyamidine reactant from one reaction vessel to another. In some cases, a water-immiscible organic solvent is used for isolation of the N-hydroxyamidine of Formula (IIa) or (IIb) and production of the 3,5-disubstituted-1,2,4-oxadiazole product. The use of a water-immiscible organic solvent allows for separation of the aqueous and organic phases of the reaction mixture, which enables a more expedient transfer of the N-hydroxyamidine reactant from one vessel to another and facilitates the recovery of the final 3,5-disubstituted-1,2,4-oxadiazole product, as set forth in greater detail below. Furthermore, in one embodiment, the water-immiscible organic solvent forms an azeotrope with water. The formation of an azeotrope facilitates removal, via e.g. evaporation or distillation, of the solvent for purposes of isolation of the intermediate oxime ester or the 3,5-disubstituted-1,2,4-oxadiazole product. Alternatively, more than one organic solvent can be used, for example, a water-immiscible solvent for production of the oxime ester intermediate of Formula (IVa) or (IVb) and a water-miscible solvent for the production of the 3,5-disubstituted-1,2,4-oxadiazole product. Non-limiting examples of suitable organic solvents include acetone, 2-butanone, ethyl acetate, isopropyl acetate, butyl acetate, chloroform, dichloromethane, diethylether, methyl-tert-butyl ether, dibutylether, anisole, tetrahydrofuran, 2-methyltetrahydrofuran, xylene, and toluene. In various embodiments, the organic solvent includes acetone, 2-butanone, tetrahydrofuran, 2-methyltetrahydrofuran, or butyl acetate. In one embodiment, the organic solvent is butyl acetate or 2-methyltetrahydrofuran.

The aqueous base comprises a chemical reagent which reacts with the acid by-product of the condensation reaction between the N-hydroxyamidine and acyl chloride. Furthermore, without being bound to any particular theory, it is believed that the aqueous base catalyzes the cyclization of the oxime ester of Formula (IVa) or (IVb) to produce the 3,5-disubstituted-1,2,4-oxadiazole of Formula (Ia) or (Ib).

"Aqueous base" is defined herein as a strong base or a base that completely or almost completely dissociates in water. The use of a strong base may advantageously result in faster reaction times. In some embodiments, the aqueous base is an alkali base comprising an alkali metal or alkaline earth metal, and which dissociates to form hydroxide ions in aqueous solution. Non-limiting examples of suitable aqueous bases include aqueous solutions of inorganic bases such as sodium hydroxide, potassium hydroxide, lithium hydroxide, calcium hydroxide, and mixtures thereof. In one embodiment, the aqueous base solution added to the reaction mixture comprises the base reagent in a concentration of from about 5% to about 60% by weight. In one exemplary embodiment, the aqueous base is an alkaline hydroxide which reacts with the acid by-product of the condensation reaction between N-hydroxyamidine and acyl chloride to form water (water forms only from the hydroxide base) and a salt.

In accordance with one embodiment, the reaction mixture optionally comprises a phase transfer catalyst. A phase transfer catalyst is a chemical reagent that facilitates the migration of a reactant from the aqueous phase into the organic phase, or vice versa. Accordingly, the use of a phase transfer catalyst may advantageously result in faster reaction times and higher conversions or yields.

In various embodiments, the phase transfer catalyst is a quaternary ammonium salt, a phosphonium salt, or a crown ether. Non-limiting examples of suitable phase transfer catalysts include tetrabutylammonium hydroxide, benzyltrimethylammonium hydroxide, tetrabutylammonium bromide, tetrabutylammonium chloride, tetrabutylammonium iodide, tetrabutylphosphonium bromide, and tetrabutylphosphonium chloride. In one embodiment, the phase transfer catalyst is tetrabutylammonium hydroxide. In one embodiment, the phase transfer catalyst is added to the reaction mixture in the form of an aqueous solution (e.g., a 40% by weight aqueous solution of the phase transfer catalyst) such that the final concentration is about 0.5-3 mol % based on acyl chloride, more preferably in a range of about 0.5-1.5 mol % or of about 1.5-2 mol % based on acyl chloride.

In one embodiment of the process, the N-hydroxyamidine of Formula (IIa) or (IIb) is dissolved in a water-immiscible organic solvent and the solution is introduced into a reaction vessel. Water, at least a portion of the aqueous base, and the optional phase transfer catalyst are added to the reaction vessel. This may be simultaneous and/or sequentially. This results in the formation of a two-phase reaction mixture, in which the N-hydroxyamidine remains dissolved in the organic phase comprising a water-immiscible organic solvent. The acyl chloride reactant of Formula (IIIa) or (IIIb) and any remaining portion of the aqueous base are added to the reaction vessel. The acyl chloride and the remaining portion of the aqueous base may be added simultaneously or sequentially. In one embodiment, the N-hydroxyamidine is added to the reaction mixture in an amount equal to or in excess of the acyl chloride on a molar basis. Additional water may be added to the reaction mixture at any time during the course of the reaction.

In some embodiments, the mixture may be agitated. In additional embodiments, the reaction could be conducted continuously, for example, in a continuous stirred-tank reactor.

In order to enhance the reaction rate and achieve acceptable reaction times, the concentration of base in the aqueous phase of the reaction mixture is preferably sufficient to achieve a pH of at least about 8, at least about 9, or at least about 10 with higher pH resulting in increased reaction rate. For example, in one embodiment, a pH of from about 12 to about 13 is a pH range resulting in an increased reaction rate. The pH of the aqueous phase may be maintained or increased during the process by addition of additional aqueous base to the reaction mixture.

The temperature of the reaction mixture is from about 25° C. to about 85° C. The temperature of the reaction mixture is in some embodiments allowed to rise as a result of the reaction exotherm, and is preferably from about 55° C. to about 75° C. The reaction may be allowed to proceed in the absence of external heat applied to the reaction mixture, although heat from an extraneous source may be supplied as needed to maintain the desired reaction temperature and rate.

The rate of addition of the acyl chloride and the remaining aqueous base is dependent on reaction scale and ability to control the temperature. For example, the rate of addition of acyl chloride may be between 30 min and 4 hours. The reaction mixture is advantageously allowed to heat as a result of the reaction exotherm, as described above, and may be maintained at from about 55° C. to about 75° C. for about 30 minutes to about 2 hours to allow the reaction to proceed to completion. Upon completion of the reaction, the aqueous and organic phases are typically allowed to separate while hot. In some embodiments, the aqueous phase may be optionally neutralized to a lower pH (e.g., pH lowered to less than about 9) to assist in subsequent formulation of the 3,5-disubstituted-1,2,4-oxadiazole product. In some embodiments, a portion of the aqueous phase is removed from the reaction mixture and the organic solvent is removed by evaporation or distillation. When the solvent level is low, the azeotrope, or pairing of the water and solvent, assists in driving out traces of solvent. The distillation may be conducted at atmospheric pressure, or under vacuum. Additional water may be added to the reaction mixture in a volume sufficient to replace the distilled solvent and to facilitate the isolation of the final product. As the solvent evaporates, the 3,5-disubstituted-1,2,4-oxadiazole product is precipitated in the aqueous layer, resulting in a slurry of solids in the aqueous layer. When substantially all of the solvent has been removed, the solid 3,5-disubstituted-1,2,4-oxadiazole product may be recovered by filtration, centrifugation, and/or decanting.

The 3,5-disubstituted-1,2,4-oxadiazole product may not consistently precipitate as a fine crystalline solid and may form beads (e.g., several mm in diameter), large irregular hard lumps, or encrusted solids on the reactor walls and agitator, which is a problem for discharging from the reactor and subsequent processing. One solution is to not remove the byproduct salt aqueous phase. However, high residual salt (e.g., NaCl) levels in the 3,5-disubstituted-1,2,4-oxadiazole product may cause problems in formulating the product.

An alternative embodiment is to use a surfactant to stabilize droplets of product (possibly a metastable melt or a very concentrated solution) and allow the droplets to solidify as a precipitate in the aqueous layer without coalescing into larger droplets which otherwise ultimately may "crash out" as the large lumps and/or encrusted solids. Suitable surfactants may be selected from the group consisting of anionic or nonionic dispersants, anionic or nonionic detergents, anionic or nonionic surfactants, and combinations thereof. Non-limiting examples of suitable surfactants include Morwet D-425 (an anionic dispersant, an alkyl naphthalene sulfonate condensate sodium salt, from AkzoNobel), Morwet D-425 and Greenworks (sodium lauryl sulfate (anionic detergent), alkyl polyglucoside (nonionic surfactant), lauramine oxide (nonionic detergent), and glycerine), Morwet D-425 and Pluronic L-35 (a surfactant, a PEG-PPG-PEG block copolymer of polyethylene glycol-polypropylene glycol-polyethylene glycol, Mn≈1900), Pluronic L-35, and Triton X-100 (a nonionic detergent, an octylphenol ethoxylate (n≈10)). In one embodiment, the surfactant is added to the reaction mixture after the reaction is substantially complete and prior to removal of at least a portion of the water-immiscible organic solvent from the reaction mixture.

In some embodiments, particularly in large scale processes or manufacturing settings with large volumes of solvent, the solvent may be recovered and recycled for re-use in the process (e.g., for use in dissolving the N-hydroxyamidine in a subsequent cycle of the process).

The N-hydroxyamidine of Formula (IIa) or (IIb) used in the preparation of 3,5-disubstituted-1,2,4-oxadiazole as described above, can be obtained from commercial sources, or may be prepared using methods known to one skilled in the art. For example, an arylamide oxime (e.g. benzamide oxime) or optionally independently substituted arylamide oxime may be prepared by reacting the corresponding aryl nitrile with hydroxylamine hydrochloride and an aqueous base. One exemplary aqueous base for this purpose is sodium hydroxide.

In some cases, to prepare an arylamide oxime starting material, hydroxylamine hydrochloride is slurried in an alcoholic solvent, such as methanol or ethanol and is combined with an equivalent molar amount of the aqueous base. In one embodiment, the aryl nitrile is added in an amount such that the hydroxylamine is in excess, for example, from about 1.01 to about 1.25 molar equivalents. The resulting reaction is mildly exothermic, and the resulting reaction mixture is heated to a temperature of from about 20° C. to about 75° C., from about 20° C. to about 65° C., from about 50° C. to about 75° C., or from about 50° C. to about 60° C. As the reaction mixture is heated, the aryl nitrile is added. The reaction mixture is then in some embodiments allowed to continue heating until the reaction is complete.

Upon completion of the reaction, the arylamide oxime product may be isolated for use in the process of the present disclosure. For example, the alcoholic solvent may be removed by distillation, leaving a reaction mixture comprising a product melt phase and an aqueous phase. While the reaction mixture is still hot, an organic solvent as described above is added to dissolve the arylamide oxime product in an organic phase. The aqueous phase may then be separated and removed. In various embodiments, the organic solvent satisfies the criteria for the organic solvent used in the production of the 3,5-disubstituted-1,2,4-oxadiazole, as set forth in detail above. Thus, the organic solvent phase comprising the dissolved arylamide oxime product may be forwarded directly to the condensation/cyclization reaction for production of the 3,5-disubstituted-1,2,4-oxadiazole without further processing. The methods described herein may be readily adapted to produce other N-hydroxyamidine compounds of Formula (IIa) or (IIb).

In an alternative embodiment, an arylamide oxime starting material (e.g., benzamide oxime) is prepared by combining and reacting the corresponding aryl nitrile with aqueous hydroxylamine (e.g., aqueous hydroxylamine includes but is not limited to aqueous hydroxylamine free base or aqueous hydroxylamine generated from the hydrochloride). By utilizing aqueous hydroxylamine, the step of neutralizing the hydroxylamine hydrochloride reactant with an aqueous base is eliminated along with the requirement of an alcoholic solvent. This provides significant capital and material savings in large-scale production processes due to the absence of an aqueous base, alcohol storage and distillation equipment and other advantages such as simplifying treatment of the aqueous waste by avoiding the production of salt in the neutralization step. In an embodiment where the arylamide oxime starting material is prepared utilizing aqueous hydroxylamine, no solvent is required. However, a solvent can be used including an alcoholic solvent, such as methanol or ethanol. In order to facilitate subsequent processing, the solvent used may be a water-immiscible organic solvent or combination of solvents selected on the basis of one or more of the criteria as set forth in detail above. For example, the organic solvent may be butyl acetate or 2-methyltetrahydrofuran. Alternatively, if the arylamide oxime starting material is prepared by combining and reacting the corresponding aryl nitrile with aqueous hydroxylamine in the absence of a solvent, after the reaction is complete, the resulting product may be dissolved in an organic solvent as described above for further processing.

The acyl chloride of Formula (IIIa) or (IIIb) (e.g., 2-thiophenecarbonyl chloride or 2-furancarbonyl chloride), used in the processes for production of 3,5-disubstituted-1,2,4-oxadiazole as described above, can be obtained from commercial sources, or may be prepared using methods known to one skilled in the art. For example, thiophene may be used to produce either 2-acetylthiophene or 2-thiophenecarboxaldehyde. Each of these may be used to produce a 2-thiophene carboxylic acid and, subsequently, 2-thiophenecarbonyl chloride. Other methods may be suitably employed to produce other acyl chloride compounds within the scope of Formula (III) or (IIIb).

The following examples are to be considered as merely illustrative, and are not intended to limit the scope of this disclosure.

EXAMPLES

Example 1

Preparation of Benzamide Oxime

Hydroxylamine hydrochloride (8.85 g, 0.126 moles) and methanol (45 mL) were charged to a 100 mL flask, followed by 51% sodium hydroxide (9.82 g, 0.125 moles). To this mixture was added benzonitrile (10.32 g, 0.100 moles), and the reaction was heated to 55-60° C. and held for 2 hours. HPLC showed that the reaction was complete by the disappearance of benzonitrile. A portion of the methanol (30 mL) was removed by distillation, deionized (DI) water was added (22 mL), and the remaining methanol was distilled at 300 torr to give two liquid phases (benzamide oxime melt and salt water). 2-Methyltetrahydrofuran (20.0 g) was added, and the aqueous salt phase was drained off to give 33.34 g of a solution of benzamide oxime in 2-methyltetrahydrofuran, 39.45% by loss on drying and HPLC. The yield of benzamide oxime was 96.5%.

Example 2

Preparation of 3-Phenyl-5-(thiophen-2-yl)-1,2,4-oxadiazole in 2-Methyltetrahydrofuran A 39.45% solution of benzamide oxime in 2-methyltetrahydrofuran (33.34 g) was charged to a 100 mL flask, followed by water (9.0 g), 40% aqueous solution of tetrabutylammonium hydroxide (1.02 g), and 51% sodium hydroxide (3.52 g, 0.045 moles). To this mixture was added 2-thiophenecarbonyl chloride (13.83 g, 0.0936 moles) and 51% sodium hydroxide (7.33 g, 0.0935 moles) simultaneously over a 30 minute period while heating to about 70° C. The reaction was complete in less than 80 minutes. The aqueous salt phase was removed, water was added (30 g), and the 2-methyltetrahydrofuran partly removed by atmospheric distillation (13.5 mL). An additional amount (32 g) of hot water was added, and the remainder of the 2-methyltetrahydrofuran was distilled out, during which time the product, 3-phenyl-5-(2-thienyl)-1,2,4-oxadiazole, precipitated. The aqueous slurry of 3-phenyl-5-(2-thienyl)-1,2,4-oxadiazole was filtered, washed with water and dried overnight in a vacuum oven to yield 3-phenyl-5-(2-thienyl)-1,2,4-oxadiazole, 20.47 g, 99.1% pure, 95.0% yield.

Example 3

Preparation of 3-Phenyl-5-(thiopheny-2-yl)-1,2,4-oxadiazole in Acetone

Benzamide oxime (5.00 g, 36.7 mmol) was dissolved in acetone (50 mL) at 0° C. The solution was stirred and 50% aqueous sodium hydroxide (4.5 mL) added. An exotherm was noted and a precipitate formed in the reaction mixture. The exotherm lasted for about 15 minutes and the slurry became thick. The solution was warmed to 20° C. and external cooling was added. The 2-thiophenecarbonyl chloride (5.36, 36.7 mmol) was added over 15 minutes maintaining the reaction mixture below 30° C. The reaction was maintained at 30° C. for 15 minutes and the slurry became thinner. The reaction mixture was cooled to room temperature and stirred for 20 additional minutes. Water (50 mL) was added and the resulting solids were stirred for 1 hour. The solids were collected by vacuum filtration, washed with water (2×50 mL) and dried on a Buchner funnel with air flow from vacuum overnight. 3-Phenyl-5-(2-thienyl)-1,2,4-oxadiazole (6.94 g, 30.4 mmol) was obtained as a white solid (83% yield).

Example 4

Preparation of Benzamide Oxime

Hydroxylamine hydrochloride (88.5 g, 1.26 moles) and methanol (450 mL) were charged to a 1000 mL flask, followed by 51% sodium hydroxide (97.7 g, 1.25 moles).

Benzonitrile (103.1 g, 1.00 moles) was added and the reaction was heated to 65-71° C. for 4 hours. HPLC showed that the reaction was complete by the disappearance of benzonitrile. A portion of the methanol (366 mL) was removed by distillation, DI water was added (200 mL), and the remaining methanol was distilled at 200 torr to give two liquid phases (benzamide oxime melt and salt water). Butyl acetate (650 mL) and DI water (100 mL) were added, and the aqueous salt phase was drained off. The butyl acetate solution was washed once with 100 mL of water to give 715.04 g of a blue-tinted cloudy solution of benzamide oxime in butyl acetate, 18.1% by loss on drying. Yield of benzamide oxime was 95.1% with a 3.4% yield of benzamide by-product.

Example 5

Preparation of Benzamide Oxime

Benzonitrile (25.0 g, 242 mmol) was added to a 250 mL flask and heated to 50° C. Aqueous hydroxylamine (50%, 20.4 g, 309 mmol) was added via a syringe pump at 0.17 mL/min (2 hours addition time). Upon completion of the addition of the 50% aqueous hydroxylamine solution, the reaction was stirred an additional 1 hour 30 minutes at 50° C. The reaction was complete and 80 mL of 2-methyltetrahydrofuran and 25 mL of water were added. The solution was mixed for 10 minutes and the layers were separated. The water white organic layer (96.3 g) was collected. Upon analysis, the organic layer contained 29.48 w/w % of the benzamide oxime product (28.4 g, 208 mmol). The yield was 86%.

Example 6

Preparation of Benzamide Oxime

Benzonitrile (50.0 g, 0.485 mol) was added to a 250 mL flask and heated to 70° C. with stirring. Deionized water (1.0 g) was added and the temperature was lined out at 70° C. Aqueous hydroxylamine (50%, 37.50 g, 34.8 ml, assay was 53.3%, 0.605 moles) was added via a syringe pump over 1.5 hours while maintaining the temperature at 70°±2° C. HPLC analysis indicated that the conversion of benzonitrile was >99% after about 2.5 hours of reaction time. The batch was heated for a total of 3.5 hours at 70° C., then was cooled to 60°

C. The batch was transferred to a 500 mL flask with 2-methyltetrahydrofuran (208.98 g), followed by 20 wt % aqueous NaCl (40.0 g). The mixture was heated to 60° C., and the phases were separated at 60° C. to give a solution of benzamide oxime in 2-methyltetrahydrofuran (281.80 g) and aqueous waste (44.61 g). The 2-methyltetrahydrofuran solution assayed for 21.73 wt % benzamide oxime.

Example 7

Preparation of 3-Phenyl-5-(thiophen-2-yl)-1,2,4-oxadiazole in Butyl Acetate

A solution of benzamide oxime (18.3%) in butyl acetate (27.30 g, 36.7 mmol) was charged to a 100 mL flask, followed by 40% aqueous tetrabutylammonium hydroxide (0.40 g), and 51% sodium hydroxide (0.86 g, 11.0 mmol). To this mixture was added 2-thiophenecarbonyl chloride (5.44 g, 36.8 mmol) and 51% sodium hydroxide (2.88 g, 36.7 mmol) simultaneously over 30 minutes while heating to about 70° C. An additional 0.66 g of 51% sodium hydroxide was added to raise the pH to 9.75. The reaction was complete in less than 2.5 hours (HPLC analysis). Hot deionized water (10 mL) was added to dissolve salts, followed by separation, washing with 10 mL of hot water and separation. Deionized water (50 mL) was added and the butyl acetate was removed by azeotropic distillation at 66-75° C. and 300 torr. The 3-phenyl-5-(thiophen-2-yl)-1,2,4-oxadiazole precipitated during the distillation. The product was discharged, filtered through a coarse glass frit, washed with water (2×15 mL), and dried overnight in a vacuum oven to give 3-phenyl-5-(thiopheny-2-yl)-1,2,4-oxadiazole (7.50 g, 88.2%); 98.6% purity.

Example 8

Preparation of 4-Chlorobenzamidoxime

A solution of 50% aqueous sodium hydroxide (2.8 g, 36.34 mmol) was mixed in methanol (20.0 mL). Hydroxylamine hydrochloride (2.55 g, 36.34 mmol) was added and the mixture stirred for 5 minutes. 4-Chlorobenzonitrile (4.0 g, 29.08 mmol) was added and the mixture heated to 60° C. The heterogeneous mixture was stirred at 60° C. for 3 hours. The mixture was poured into water (30 mL) and solids dissolved and a precipitate appeared. The methanol was removed at reduced pressure and remaining solids collected by vacuum filtration. The solids were washed with water (2×10 mL). The 4-chlorobenzamidoxime (4.38 g, 25.6 mmol) was obtained as a white solid. (88% yield).

Example 9

Preparation of 3-(4-Chlorophenyl)-5-(2-thienyl)-1,2,4-oxadiazole

The 4-chlorobenzamidoxime (1.00 g, 5.8 mmol) was dissolved in 2-methyltetrahydrofuran (10.0 mL) and water (1.0 mL). A 40% aqueous solution of benzyltrimethylammonium hydroxide (100 uL) was added and the solution heated to 50° C. A 50% aqueous solution of sodium hydroxide (720 mg, 9.00 mmol) and 2-thiophenecarbonyl chloride (939.0 mg, 6.4 mmol) were added dropwise simultaneously over 15 minutes. The temperature of the mixture warmed to 70° C. The mixture was cooled to room temperature and water (40 mL) added. Solids formed and the 2-methyltetrahydrofuran was removed at reduced pressure. The solids were isolated by vacuum filtration. The 3-(4-chlorophenyl)-5-(2-thienyl)-1,2,4-oxadiazole (1.32 g, 5.0 mmol) was obtained as a white solid. (86% yield).

Example 10

Preparation of 3-(4-Chlorophenyl)-5-(2-furanyl)-1,2,4-oxadiazole

The 4-chlorobenzamidoxime (1.24 g, 7.25 mmol) was dissolved in 2-methyltetrahydrofuran (10.0 mL) and water (1.0 mL). A 40% aqueous solution of benzyltrimethylammonium hydroxide (100 uL) and 50% aqueous solution of sodium hydroxide (736 mg, 9.20 mmol) were added. The mixture was stirred and a precipitate formed. Furoyl chloride (1.24 g, 7.25 mmol) was added dropwise and an exotherm was noted. The mixture was stirred at 70° C. for 1 hour and cooled to room temperature. The solution was poured into water (25 mL) and the 2-methyltetrahydrofuran removed at reduced pressure. The resulting solids were isolated by vacuum filtration. The 3-(4-chlorophenyl)-5-(2-furanyl)-1,2,4-oxadiazole (1.22 g, 4.94 mmol) was obtained as a white solid. (68% yield).

Example 11

Preparation of 3-Phenyl-5-(2-furanyl)-1,2,4-oxadiazole

Benzamide oxime (2.00 g, 14.7 mmol) and a 40% aqueous solution of benzyltrimethylammonium hydroxide (100 uL) were combined in 2-methyltetrahydrofuran (20 mL) and water (2 mL). The solution was warmed to 50° C. and 50% aqueous solution of sodium hydroxide (1.52 g, 19.1 mmol) and 2-furoyl chloride (2.00 g, 15.3 mmol) were added dropwise simultaneously over 10 min. The pot temperature rose to 74° C. The mixture was stirred at 60° C. for 48 hours and the solids dissolved. The mixture was cooled to room temperature and poured into water (25 mL). The 2-methyltetrahydrofuran was removed at reduced pressure and solids formed in the aqueous solution. The solids were collected by vacuum filtration. 3-phenyl-5-(2-furanyl)-1,2,4-oxadiazole (2.33 g, 9.5 mmol) was obtained as a white solid. (64% yield).

Example 12

Preparation of 3-Phenyl-5-(thiophen-2-yl)-1,2,4-oxadiazole

A solution of benzamide oxime (24.92%) in 2-methyl THF (67.53 g, 124 mmoles) was charged to a 500 mL flask, followed by DI water (20.0 g), 55% aqueous tetrabutylammonium hydroxide (0.94 g), and 50% sodium hydroxide (0.96 g, 12 mmoles). To this mixture was added 2-thiophenecarbonyl chloride (17.77 g, 120 mmoles) and 50% sodium hydroxide (9.60 g, 120 mmoles) simultaneously over 30 minutes while heating to about 70° C. The reaction was complete is less than one hour. The temperature was reduced to 60° C., and the pH of the aqueous phase was neutralized to 7.61, and was drained off to waste. A hot solution of 1.25 g of Morwet D-425 in 100 ml DI water was added to the mixture, and the 2-phase mixture was heated to distill off the 2-methyltetrahydrofuran/water azeotrope (boiling point 71° C.). Additional water (150 ml) was pumped into the reactor flask over about 15 minutes, once the 2-methyltetrahydrofuran began to distill out. While maintaining good agitation, the pot temperature reached 100.5° C. (vapor temperature 97° C.). The slurry was cooled and filtered using a coarse glass frit. The scale was scraped off the agitator and combined with the wet cake; the scale was only about 3% of total product. The combined wet cake was washed with hot DI water (3×50 ml) and suction-dried for 5 minutes to give a 3-phenyl-5-(thiophen-2-yl)-1,2,4-oxadiazole wet cake, 34.80 g. The loss on drying of the wet cake was 20.13%. The assay of the dried 3-phenyl-5-(thiophen-2-yl)-1,2,4-oxadiazole was 96.12%, and the residual chloride was <200 ppm.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above products and methods without departing from the scope of the disclosure, it is intended that all matter contained in the above description shall be interpreted as illustrative and not in a limiting sense.

What is claimed is:

1. A process for preparing a 3,5-disubstituted 1,2,4-oxadiazole of Formula (Ia) or (Ib), or a salt thereof,

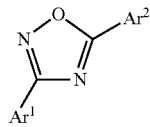
(Ia)

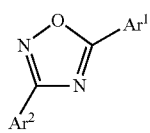
(Ib)

the process comprising reacting an N-hydroxyamidine of Formula (IIa) or (IIb), respectively, or a tautomeric form thereof,

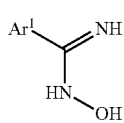
(IIa)

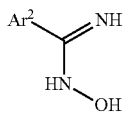
(IIb)

with an acyl chloride of Formula (IIIa) or (IIIb), respectively,

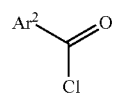
(IIIa)

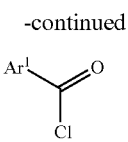
(IIIb)

in a reaction mixture comprising an organic phase and an aqueous phase,
wherein the reaction mixture comprises a water-immiscible organic solvent and an aqueous base,
wherein the temperature of the reaction mixture is no greater than about 85° C.;
and wherein $Ar^1$ is selected from the group consisting of phenyl, pyridyl, pyrazyl, oxazolyl or isoxazolyl, each of which can be optionally independently substituted with one or more substituents selected from the group consisting of halogen, $CF_3$, $CH_3$, $OCF_3$, $OCH_3$, CN and C(H)O; and
$Ar^2$ is selected from the group consisting of is thienyl, furanyl, oxazolyl or isoxazolyl, each of which can be optionally independently substituted with one or more substituents selected from the group consisting of fluorine, chlorine, $CH_3$, and $OCF_3$.

2. The process of claim 1 wherein the process comprises reacting an N-hydroxyamidine of Formula (IIa), or a tautomeric form thereof, with an acyl chloride of Formula (IIIa) to form a 3,5-disubstituted 1,2,4-oxadiazole of Formula (Ia), or a salt thereof.

3. The process of claim 1 wherein the process comprises reacting an N-hydroxyamidine of Formula (IIb), or a tautomeric form thereof, with an acyl chloride of Formula (IIb) to form a 3,5-disubstituted 1,2,4-oxadiazole of Formula (Ib), or a salt thereof.

4. The process of claim 1 wherein the reaction mixture further comprises a phase transfer catalyst.

5. The process of claim 4 wherein the phase transfer catalyst is selected from the group consisting of quaternary ammonium salts, phosphonium salts, and crown ethers.

6. The process of claim 4 wherein the phase transfer catalyst is selected from the group consisting of tetrabutylammonium hydroxide, tetrabutylammonium bromide, tetrabutylammonium fluoride, tetrabutylammonium iodide, tetrabutylphosphonium bromide, tetrabutylphosphonium chloride, and benzyltrimethylammonium hydroxide.

7. The process of claim 6 wherein the phase transfer catalyst is tetrabutylammonium hydroxide.

8. The process of claim 1 wherein the water-immiscible organic solvent solubilizes the N-hydroxyamidine and the 3,5-disubstituted-1,2,4-oxadiazole.

9. The process claim 1 wherein the water-immiscible organic solvent forms an azeotrope with water.

10. The process of claim 1 wherein the water-immiscible organic solvent is selected from the group consisting of 2-methyltetrahydrofuran and butyl acetate.

11. The process of claim 10 wherein the water-immiscible organic solvent is 2-methyltetrahydrofuran.

12. The process of claim 1 wherein the aqueous base is selected from the group consisting of sodium hydroxide, potassium hydroxide, lithium hydroxide, and calcium hydroxide.

13. The process of claim 12 wherein the aqueous base is selected from the group consisting of sodium hydroxide and potassium hydroxide.

14. The process of claim 1 wherein the pH of the aqueous phase is greater than about 8.

15. The process of claim 1 wherein the pH of the aqueous phase is greater than about 10.

16. The process of claim 1 wherein the pH of the aqueous phase is increased or maintained by adding additional aqueous base to the reaction mixture.

17. The process of claim 1 wherein the temperature of the reaction mixture is maintained at from about 55° C. to about 75° C.

18. The process of claim 1 wherein the N-hydroxyamidine is dissolved in the water-immiscible organic solvent prior to adding the acyl chloride to form the reaction mixture.

19. The process of claim 1 further comprising recovering the 3,5-disubstituted-1,2,4-oxadiazole from the reaction mixture as a precipitate from an aqueous layer after removal of at least a portion of the water-immiscible organic solvent from the reaction mixture.

20. The process of claim 19 further comprising adding a surfactant to the reaction mixture.

21. The process of claim 20 wherein the surfactant added to the reaction mixture stabilizes droplets of the 3,5-disubstituted-1,2,4-oxadiazole in an aqueous layer and allows the droplets to solidify without coalescing into larger droplets.

22. The process of claim 20 wherein the surfactant is added to the reaction mixture prior to removal of at least a portion of the water-immiscible organic solvent from the reaction mixture.

23. The process of claim 20 wherein the surfactant is added to the reaction mixture after the reaction is substantially complete.

24. The process of claim 20 wherein the surfactant is selected from the group consisting of anionic or nonionic dispersants, anionic or nonionic detergents, anionic or nonionic surfactants, and combinations thereof.

25. The process of claim 1 wherein the reaction of the N-hydroxyamidine and the acyl chloride produces an oxime ester intermediate of Formula (IVa) or (IVb), a salt thereof, or a tautomeric form thereof,

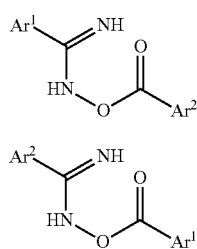

wherein Ar$^1$ and Ar$^2$ are defined as in claim 1.

26. The process of claim 25 wherein the water-immiscible organic solvent solubilizes the N-hydroxyamidine, the oxime ester intermediate, and the 3,5-disubstituted 1,2,4-oxadiazole.

27. The process of claim 25 wherein the oxime ester intermediate is isolated prior to formation of the 3,5-disubstituted 1,2,4-oxadiazole.

28. The process of claim 1 wherein the N-hydroxyamidine is a benzamide oxime formed by reacting a substituted or unsubstituted benzonitrile and hydroxylamine hydrochloride in an alcoholic solvent with sodium hydroxide and the benzamide oxime is separated from the alcohol solvent and subsequently dissolved in a solvent selected from the group consisting of 2-methyltetrahydrofuran and butyl acetate.

29. The process of claim 1 wherein the N-hydroxyamidine is a benzamide oxime formed by reacting a substituted or unsubstituted benzonitrile and hydroxylamine and the formed benzamide oxime is dissolved in a solvent selected from the group consisting of 2-methyltetrahydrofuran and butyl acetate.

30. The process of claim 29 wherein the reaction to form the benzamide oxime is carried out at a temperature of from about 20° C. to about 65° C.

31. The process of claim 1 wherein the N-hydroxyamidine is a benzamide oxime formed by combining and reacting a substituted or unsubstituted benzonitrile and aqueous hydroxylamine.

32. The process of claim 31 wherein the substituted or unsubstituted benzonitrile and aqueous hydroxylamine are combined and reacted in the absence of a water-immiscible organic solvent.

33. The process of claim 31 wherein the substituted or unsubstituted benzonitrile and aqueous hydroxylamine are combined and reacted in a water-immiscible organic solvent and the benzamide oxime is dissolved in the solvent.

34. The process as set forth in claim 33 wherein the water-immiscible organic solvent is selected from the group consisting of 2-methyltetrahydrofuran and butyl acetate.

35. The process of claim 1 wherein the process comprises:
  (1) introducing the N-hydroxyamidine into a reaction vessel as a solution dissolved in the water-immiscible organic solvent;
  (2) adding a portion of the aqueous base, and optionally a phase transfer catalyst, to the reaction vessel;
  (3) adding the acyl chloride to the reaction vessel to form the reaction mixture; and
  (4) adding additional aqueous base to the reaction mixture in the reaction vessel.

36. The process of claim 35 wherein the water-immiscible organic solvent is selected from the group consisting of 2-methyltetrahydrofuran and butyl acetate.

37. The process of claim 35 wherein the acyl chloride and the additional aqueous base are added to the reaction vessel simultaneously.

38. The process of claim 35 wherein the acyl chloride and the additional aqueous base are added to the reaction vessel sequentially.

39. The process of claim 1 wherein Ar$^1$ is unsubstituted phenyl.

40. The process of claim 1 wherein Ar$^1$ is monosubstituted phenyl wherein the substituent is a halogen.

41. The process of claim 1 wherein Ar$^1$ is a disubstituted chloroalkylphenyl.

42. The process of claim 1 wherein Ar$^2$ is substituted or unsubstituted thiophene or furan.

43. The process of claim 42 wherein Ar$^2$ is unsubstituted thiophene.

44. The process of claim 1 wherein the 3,5-disubstituted-1,2,4-oxadiazole is 3-phenyl-5-(2-thienyl)-1,2,4-oxadiazole, or a salt thereof.

45. The process of claim 28 wherein the alcoholic solvent is methanol.

* * * * *

UNITED STATES PATENT AND TRADEMARK OFFICE
CERTIFICATE OF CORRECTION

| | | |
|---|---|---|
| PATENT NO. | : 9,040,711 B2 | Page 1 of 1 |
| APPLICATION NO. | : 13/933616 | |
| DATED | : May 26, 2015 | |
| INVENTOR(S) | : William Harold Miller et al. | |

It is certified that error appears in the above-identified patent and that said Letters Patent is hereby corrected as shown below:

In the Claims

Column 16, Claim 3, Line 33: "Formula (IIb)" should read -- Formula (IIIb) --

Signed and Sealed this
Twenty-fourth Day of November, 2015

Michelle K. Lee
*Director of the United States Patent and Trademark Office*